(12) United States Patent
Zhou et al.

(10) Patent No.: US 10,639,265 B2
(45) Date of Patent: May 5, 2020

(54) PRESERVATIVE-FREE TOOTHPASTE FOR CHILDREN

(71) Applicant: Suzhou Fresh Health Technology Co., Ltd, Suzhou, Jiangsu (CN)

(72) Inventors: Yanping Zhou, Jiangsu (CN); Jianlin Mao, Jiangsu (CN)

(73) Assignee: SUZHOU FRESH HEALTH TECHNOLOGY CO., LTD, Suzhou (CN)

( * ) Notice: Subject to any disclaimer, the term of this patent is extended or adjusted under 35 U.S.C. 154(b) by 0 days.

(21) Appl. No.: 16/504,234

(22) Filed: Jul. 6, 2019

(65) Prior Publication Data
US 2020/0093727 A1    Mar. 26, 2020

(30) Foreign Application Priority Data

Aug. 16, 2018   (CN) .......................... 2018 1 0935609

(51) Int. Cl.
| A61K 8/67 | (2006.01) |
| A61K 8/34 | (2006.01) |
| A61K 8/46 | (2006.01) |
| A61K 8/73 | (2006.01) |
| A61K 8/55 | (2006.01) |
| A61K 8/86 | (2006.01) |
| A61Q 11/00 | (2006.01) |

(52) U.S. Cl.
CPC .............. *A61K 8/676* (2013.01); *A61K 8/345* (2013.01); *A61K 8/463* (2013.01); *A61K 8/55* (2013.01); *A61K 8/678* (2013.01); *A61K 8/731* (2013.01); *A61K 8/737* (2013.01); *A61K 8/86* (2013.01); *A61Q 11/00* (2013.01); *A61K 2800/30* (2013.01)

(58) Field of Classification Search
CPC .............. A61K 7/18; A61K 8/85; A61L 15/00
USPC ............................................ 424/49, 52, 401
See application file for complete search history.

(56) References Cited

U.S. PATENT DOCUMENTS 5,869,029 A  *  2/1999  Graff-Andersen ....... A61K 8/60
                                                              252/175
2006/0286044 A1 * 12/2006  Robinson ............... A61K 8/345
                                                               424/49

FOREIGN PATENT DOCUMENTS

| CN | 103385805 A | 11/2013 |
| CN | 105534867 A | 5/2016 |
| CN | 106473936 A | 3/2017 |
| CN | 106581159 A | 4/2017 |
| CN | 107625662 A | 1/2018 |

* cited by examiner

*Primary Examiner* — Walter E Webb
(74) *Attorney, Agent, or Firm* — Wayne & Ken, LLC; Tony Hom

(57) ABSTRACT

The present invention discloses preservative-free toothpaste for children. The composition forming the preservative-free toothpaste for children consists of vitamin, calcium glycerophosphate, xylitol, sorbitol, polyethylene glycol, cellulose, hydroxypropyl guar gum, sodium lauryl sulfate, flavors and deionized water. The composition contains, by weight percentage, 0.01-0.06% of vitamin, 0.1-0.5% calcium glycerophosphate and 0.1-1% of xylitol. The vitamin comprises both vitamin E and vitamin C. In the present invention, vitamin E, vitamin C, calcium glycerophosphate and xylitol are combined in a certain proportion. The vitamin nourishes the children's tender gums. The calcium glycerophosphate provides calcium supplementation to the teeth. The xylitol has a reduced content of sugar, which prevents tooth decay and strengthens the teeth.

2 Claims, No Drawings

PRESERVATIVE-FREE TOOTHPASTE FOR CHILDREN

CROSS-REFERENCE TO RELATED APPLICATIONS

This application claims the benefit of priority from Chinese Patent Application No. CN201810935609.6, filed on Aug. 16, 2018. The content of the aforementioned application, including any intervening amendments thereto, is incorporated herein by reference in its entirety.

TECHNICAL FIELD

The present invention relates to preservative-free toothpaste for children, relating to the field of daily necessities.

BACKGROUND OF THE PRESENT INVENTION

Definition of Terms

Preservative-free toothpaste for children: toothpaste for children produced from food-grade material without any preservatives. Such toothpaste is safer because of no harmfulness of preservatives. The effective combination of components nourishes the children's gums and also strengthens their teeth.

Preservatives are natural or synthetic chemical components used to slow down decomposition caused by microbial growth or by chemical changes. They may be agents used to inhibit substance decomposition. Preservatives can continuously inhibit the growth of microbes using decomposed substance as the metabolic substrate. Importantly, preservatives can inhibit the most possible decomposition in different conditions, and can continuously inhibit the decomposition particularly in the case of insufficient sterilization.

Toothpaste, as a daily necessity, is used to brush the teeth to maintain oral hygiene, and is safe for use in the human bodies. With the improvement of the living standard, the requirements on the quality of toothpaste are gradually increased. In terms of performance, generally, toothpaste is expected to: (1) be able to remove the film and plaque on the surface of the teeth, without damaging enamel and dentin; (2) be good at cleaning the oral cavity and its surrounding; (3) be non-toxic and no stimulating effect on oral mucosa; and (4) smell good, taste good, and feel fresh and cool after brushing the teeth. The existing toothpaste usually contains preservatives. The preservatives are harmless to human health as long as the content of preservatives is within a safe range. However, preservative-free toothpaste is safer since children have a weak immune system. Children have tender enamel and sensitive oral mucosa and may swallow toothpaste due to low self-control. Therefore, requirements on the safety of toothpaste for children than that for adults should be higher.

SUMMARY OF THE PRESENT INVENTION

A technical problem to be solved in the present invention is to provide preservative-free toothpaste for children which, by considering the characteristics of teeth and the oral cavity of children, solves the difficulties in children's oral-caring due to tender enamel and sensitive oral mucosa.

In order to realize the above technical effect, the following technical solution is employed in the present invention.

Preservative-free toothpaste for children is provided. The composition forming the preservative-free toothpaste for children consists of vitamin, calcium glycerophosphate, xylitol, sorbitol, polyethylene glycol, cellulose, hydroxypropyl guar gum, sodium lauryl sulfate, flavors and deionized water. The composition contains, by weight percentage, 0.01-0.06% of vitamin, 0.1-0.5% calcium glycerophosphate and 0.1-1% of xylitol. The vitamin comprises both vitamin E and vitamin C.

Further, the composition consists of following components: by weight percentage, 0.01-0.06% of vitamin, 0.1-0.5% calcium glycerophosphate, 0.1-1% of xylitol, 60-68% of sorbitol, 1-3% of polyethylene glycol, 0.8-1.3% of cellulose, 0.3-1% of hydroxypropyl guar gum, 0.5-1% of sodium lauryl sulfate, 0.5-1% of flavors, with the balance being deionized water.

Further, the content of the vitamin E is 40-70% in the total amount of vitamin and the content of the vitamin C is 30-50% in the total amount of vitamin.

Compared with the prior art, the present invention has the following beneficial effects.

The solution of the present invention is provided from the prospective of safety and nutrition. Vitamin E, vitamin C, calcium glycerophosphate and xylitol are combined in a certain proportion. The vitamin nourishes the children's tender gums. The calcium glycerophosphate provides calcium supplementation to the teeth. The xylitol has a reduced content of sugar, which prevents tooth decay and strengthens the teeth. The components of the composition contain no preservative. Furthermore, it is low foaming and safer in use.

The foregoing description is merely an overview of the technical solution of the present invention. The present invention may be implemented according to what is described here, in order to better understand the technical solution of the present invention. Furthermore, to further understand the above and other purposes, features and advantages of the present invention, the present invention will be further described below by embodiments. Apparently, the described embodiments are only some, but not all, of the embodiments of the present invention.

DETAILED DESCRIPTION OF THE PRESENT INVENTION

Preservative-free toothpaste for children is provided. The composition consists of following components: by weight percentage, 0.01-0.06% of vitamin, 0.1-0.5% calcium glycerophosphate, 0.1-1% of xylitol, 60-68% of sorbitol, 1-3% of polyethylene glycol, 0.8-1.3% of cellulose, 0.3-1% of hydroxypropyl guar gum, 0.5-1% of sodium lauryl sulfate, 0.5-1% of flavors, with the balance being deionized water. Preferably, the content of the vitamin E is 40-70% in the total amount of vitamin and the content of the vitamin C is 30-50% in the total amount of vitamin.

The method for preparing the preservative-free toothpaste for children in this embodiment comprises steps of: weighing the above raw material components in a certain proportion; dispersing and mixing them in the pre-dispersing kettle; feeding the liquid mixture into the paste kettle by turning on its vacuum pump; turning on the scraper, the stirrer and the colloid mill, and after 50 min, successively turning off the colloid mill, the stirrer and the scraper; and releasing the vacuum to obtain the preservative-free toothpaste for children.

The preservative-free toothpaste for children in the present invention has a rational proportion of components, the vitamin nourishes the children's tender gums, the calcium glycerophosphate provides calcium supplementation to the teeth, and the xylitol has a reduced content of sugar, which prevents tooth decay and strengthens the teeth. The composition contains no preservative and it is low foaming. After long-term use of products containing this composition, the gums can be nourished and the teeth can be strengthened. It is harmless and safer. Furthermore, by the addition of sorbitol, polyethylene glycol, cellulose, hydroxypropyl guar gum, sodium lauryl sulfate and flavors, the paste of the present invention is stable, smooth and bright, and tastes good; and the paste has exquisite foam, and it is easy for children to clear off the foam.

The present invention is not limited to the above specific implementations. Various modifications made, based on the concept, by a person of ordinary skill in the art without paying any creative effort shall fall into the protection scope of the present invention.

What is claimed is:

1. Preservative-free toothpaste for children, wherein the composition forming the preservative-free toothpaste for children consists of vitamin E, vitamin C, calcium glycerophosphate, xylitol, sorbitol, polyethylene glycol, cellulose, hydroxypropyl guar gum, sodium lauryl sulfate, flavors and deionized water; the composition contains, by weight percentage, 0.004-0.042% vitamin E, 0.003-0.03% vitamin C, 0.1-0.5% calcium glycerophosphate and 0.1-1% of xylitol, wherein a weight ratio of vitamin E to vitamin C ranges from 0.8 to 2.3.

2. The preservative-free toothpaste for children according to claim 1, wherein the composition consists of following components: by weight percentage, 0.01-0.06% of vitamin, 0.1-0.5% calcium glycerophosphate, 0.1-1% of xylitol, 60-68% of sorbitol, 1-3% of polyethylene glycol, 0.8-1.3% of cellulose, 0.3-1% of hydroxypropyl guar gum, 0.5-1% of sodium lauryl sulfate, 0.5-1% of flavors, with the balance being deionized water.

* * * * *